(12) United States Patent
Guyer et al.

(10) Patent No.: US 8,043,377 B2
(45) Date of Patent: Oct. 25, 2011

(54) IMPLANTABLE INTERVERTEBRAL FUSION DEVICE

(75) Inventors: Richard D. Guyer, Dallas, TX (US); Jack E. Zigler, Dallas, TX (US); Randall F. Lee, Arlington, TX (US); Cameron Clokie, Toronto (CA)

(73) Assignee: Osprey Biomedical, Inc., Wilmington, DE (US)

( * ) Notice: Subject to any disclaimer, the term of this patent is extended or adjusted under 35 U.S.C. 154(b) by 392 days.

(21) Appl. No.: 11/469,851

(22) Filed: Sep. 2, 2006

(65) Prior Publication Data
US 2008/0097610 A1 Apr. 24, 2008

(51) Int. Cl.
*A61F 2/44* (2006.01)
(52) U.S. Cl. .................................. 623/17.11
(58) Field of Classification Search ........... 606/61, 606/297, 279; 623/17.11–17.16
See application file for complete search history.

(56) References Cited

U.S. PATENT DOCUMENTS

| | | |
|---|---|---|
| 2,621,145 A | 12/1952 | Sano |
| 3,848,601 A | 11/1974 | Ma et al. |
| 4,011,602 A | 3/1977 | Rybicki et al. |
| 4,059,115 A | 11/1977 | Jumashev et al. |
| 4,172,128 A | 10/1979 | Thiele et al. |
| 4,206,516 A | 6/1980 | Pillar |
| 4,222,128 A | 9/1980 | Tomonaga et al. |
| 4,237,559 A | 12/1980 | Borom |
| 4,294,753 A | 10/1981 | Urist |
| 4,309,488 A | 1/1982 | Heide et al. |
| 4,344,190 A | 8/1982 | Lee et al. |
| 4,394,370 A | 7/1983 | Jefferies |
| 4,430,760 A | 2/1984 | Smestad |
| 4,440,750 A | 4/1984 | Glowacki et al. |
| 4,472,840 A | 9/1984 | Jefferies |
| 4,485,097 A | 11/1984 | Bell |
| 4,501,269 A | 2/1985 | Bagby |
| 4,604,995 A | 8/1986 | Stephens et al. |
| 4,610,692 A | 9/1986 | Eitenmuller et al. |
| 4,625,722 A | 12/1986 | Murray |
| 4,626,392 A | 12/1986 | Kondo et al. |
| 4,627,434 A | 12/1986 | Murray |
| 4,627,853 A | 12/1986 | Campbell et al. |
| 4,636,217 A | 1/1987 | Ogilvie et al. |
| 4,645,503 A | 2/1987 | Lin et al. |
| 4,654,314 A | 3/1987 | Takagi et al. |
| 4,654,464 A | 3/1987 | Mittelmeier et al. |
| 4,678,470 A | 7/1987 | Nashef et al. |

(Continued)

FOREIGN PATENT DOCUMENTS

DE 29 10 627 9/1980

(Continued)

OTHER PUBLICATIONS

Shrikar Bondre et al., "Biodegradable Foam Coating of Cortical Allografts," Tissue Engineering, vol. 6, pp. 217-227, 2000.

(Continued)

*Primary Examiner* — Eduardo C Robert
*Assistant Examiner* — Mary Hoffman
(74) *Attorney, Agent, or Firm* — Novel IP

(57) ABSTRACT

The present invention relates to an implantable intervertebral fusion device for use when surgical fusion of vertebral bodies is indicated. The implant is comprised of bone conforming in size and shape with the end plates of the adjacent vertebrae and has a wedge-shaped profile with a plurality of footings and grooves located on the top and bottom surfaces.

23 Claims, 8 Drawing Sheets

U.S. PATENT DOCUMENTS

| | | | |
|---|---|---|---|
| 4,687,675 A | 8/1987 | Nakano et al. | |
| 4,714,469 A | 12/1987 | Kenna | |
| 4,722,870 A | 2/1988 | White | |
| 4,728,570 A | 3/1988 | Ashman et al. | |
| 4,743,259 A | 5/1988 | Bolander et al. | |
| 4,745,914 A | 5/1988 | Frey et al. | |
| 4,755,184 A | 7/1988 | Silverberg | |
| 4,781,721 A | 11/1988 | Grundei | |
| 4,789,663 A | 12/1988 | Wallace et al. | |
| 4,820,305 A | 4/1989 | Harms et al. | |
| 4,834,757 A | 5/1989 | Brantigan | |
| 4,858,603 A | 8/1989 | Clemow et al. | |
| 4,863,472 A | 9/1989 | Tormala et al. | |
| 4,863,477 A * | 9/1989 | Monson | 623/17.12 |
| 4,865,603 A | 9/1989 | Noiles | |
| 4,877,020 A | 10/1989 | Vich | |
| 4,878,915 A | 11/1989 | Brantigan | |
| 4,902,296 A | 2/1990 | Bolander et al. | |
| 4,917,703 A | 4/1990 | Albrektsson | |
| 4,932,973 A | 6/1990 | Gendler | |
| 4,936,848 A | 6/1990 | Bagby | |
| 4,950,295 A | 8/1990 | Weigum et al. | |
| 4,950,296 A | 8/1990 | McIntyre | |
| 4,961,740 A | 10/1990 | Ray et al. | |
| 4,969,906 A | 11/1990 | Kronman | |
| 4,975,526 A | 12/1990 | Kuberasampath et al. | |
| 4,976,738 A | 12/1990 | Frey et al. | |
| 4,994,084 A | 2/1991 | Brennan | |
| 5,002,583 A | 3/1991 | Pitaru et al. | |
| 5,015,247 A | 5/1991 | Michelson | |
| 5,026,373 A | 6/1991 | Ray et al. | |
| 5,053,049 A | 10/1991 | Campbell | |
| 5,055,104 A | 10/1991 | Ray | |
| 5,061,286 A | 10/1991 | Lyle | |
| 5,061,287 A | 10/1991 | Feiler | |
| 5,062,850 A | 11/1991 | MacMillan et al. | |
| 5,067,962 A | 11/1991 | Campbell et al. | |
| 5,073,373 A | 12/1991 | O'Leary et al. | |
| 5,078,746 A | 1/1992 | Garner | |
| 5,092,887 A | 3/1992 | Gendler | |
| 5,092,891 A | 3/1992 | Kummer et al. | |
| 5,092,892 A | 3/1992 | Ashby | |
| 5,092,893 A | 3/1992 | Smith | |
| 5,112,354 A | 5/1992 | Sires | |
| 5,133,718 A | 7/1992 | Mao | |
| 5,133,755 A | 7/1992 | Brekke | |
| 5,141,510 A | 8/1992 | Takagi et al. | |
| 5,152,791 A | 10/1992 | Hakamatsuka et al. | |
| 5,162,114 A | 11/1992 | Kuberasampath et al. | |
| 5,171,275 A | 12/1992 | Ling et al. | |
| 5,192,327 A | 3/1993 | Brantigan | |
| 5,211,664 A | 5/1993 | Tepic et al. | |
| 5,236,456 A | 8/1993 | O'Leary et al. | |
| 5,258,029 A | 11/1993 | Chu et al. | |
| 5,275,954 A | 1/1994 | Wolfinbarger et al. | |
| 5,281,226 A | 1/1994 | Davydov et al. | |
| 5,282,861 A | 2/1994 | Kaplan | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,300,077 A | 4/1994 | Howell | |
| 5,306,302 A | 4/1994 | Bauer et al. | |
| 5,306,303 A | 4/1994 | Lynch | |
| 5,306,304 A | 4/1994 | Gendler | |
| 5,306,308 A | 4/1994 | Gross et al. | |
| 5,306,309 A | 4/1994 | Wagner et al. | |
| 5,314,476 A | 5/1994 | Prewett et al. | |
| 5,320,644 A | 6/1994 | Baumgartner | |
| 5,329,846 A | 7/1994 | Bonutti | |
| 5,330,826 A | 7/1994 | Taylor et al. | |
| 5,346,492 A | 9/1994 | Morgan | |
| 5,366,508 A | 11/1994 | Brekke | |
| 5,376,120 A | 12/1994 | Sarver et al. | |
| 5,383,932 A | 1/1995 | Wilson et al. | |
| 5,401,269 A | 3/1995 | Buttner-Janz et al. | |
| 5,405,390 A | 4/1995 | O'Leary et al. | |
| 5,405,391 A | 4/1995 | Hednerson et al. | |
| 5,423,817 A | 6/1995 | Lin | |
| 5,425,768 A | 6/1995 | Carpenter et al. | |
| 5,425,769 A | 6/1995 | Snyders, Jr. | |
| 5,425,770 A | 6/1995 | Piez et al. | |
| 5,425,772 A | 6/1995 | Brantigan | |
| 5,433,751 A | 7/1995 | Christel et al. | |
| 5,439,684 A | 8/1995 | Prewett et al. | |
| 5,443,514 A | 8/1995 | Steffee | |
| 5,458,638 A | 10/1995 | Kuslich et al. | |
| 5,484,437 A | 1/1996 | Michelson | |
| 5,484,601 A | 1/1996 | O'Leary et al. | |
| 5,489,307 A | 2/1996 | Kuslich et al. | |
| 5,489,308 A | 2/1996 | Kuslich et al. | |
| 5,492,697 A | 2/1996 | Boyan et al. | |
| 5,501,706 A | 3/1996 | Arenberg | |
| 5,507,813 A | 4/1996 | Dowd et al. | |
| 5,510,396 A | 4/1996 | Prewett et al. | |
| 5,514,180 A | 5/1996 | Heggeness et al. | |
| 5,516,532 A | 5/1996 | Atala et al. | |
| 5,522,899 A | 6/1996 | Michelson | |
| 5,531,791 A | 7/1996 | Wolfinbarger, Jr. | |
| 5,534,030 A | 7/1996 | Navarro et al. | |
| 5,545,222 A | 8/1996 | Bonutti | |
| 5,549,679 A | 8/1996 | Kuslich | |
| 5,554,191 A | 9/1996 | Lahille et al. | |
| 5,554,192 A | 9/1996 | Crowninshield | |
| 5,556,379 A | 9/1996 | Wolfinbarger | |
| 5,556,430 A | 9/1996 | Gendler | |
| 5,569,308 A | 10/1996 | Sottosanti | |
| 5,570,706 A | 11/1996 | Howell | |
| 5,571,190 A | 11/1996 | Ulrich et al. | |
| 5,571,192 A | 11/1996 | Schonhoffer | |
| 5,585,116 A | 12/1996 | Boniface et al. | |
| 5,591,235 A | 1/1997 | Kuslich | |
| 5,593,409 A | 1/1997 | Michelson | |
| 5,603,716 A | 2/1997 | Morgan et al. | |
| 5,607,474 A | 3/1997 | Athanasiou et al. | |
| 5,609,635 A | 3/1997 | Michelson | |
| 5,609,636 A | 3/1997 | Kohrs et al. | |
| 5,609,637 A | 3/1997 | Biedermann et al. | |
| 5,645,598 A | 7/1997 | Brosnahan, III | |
| 5,658,337 A | 8/1997 | Kohrs et al. | |
| 5,658,351 A | 8/1997 | Dudasik et al. | |
| 5,665,120 A | 9/1997 | Ohtsuka et al. | |
| 5,676,699 A | 10/1997 | Gogolewski et al. | |
| 5,683,394 A | 11/1997 | Rinner | |
| 5,683,463 A | 11/1997 | Godefroy et al. | |
| 5,683,464 A | 11/1997 | Wagner et al. | |
| 5,697,981 A | 12/1997 | Ison et al. | |
| 5,702,449 A | 12/1997 | McKay | |
| 5,702,453 A | 12/1997 | Rabbe et al. | |
| 5,702,455 A | 12/1997 | Saggar | |
| 5,709,683 A | 1/1998 | Bagby | |
| 5,716,415 A | 2/1998 | Steffee | |
| 5,722,977 A | 3/1998 | Wilhelmy | |
| 5,725,579 A | 3/1998 | Fages et al. | |
| 5,725,813 A | 3/1998 | Nies | |
| 5,728,159 A | 3/1998 | Stroever et al. | |
| 5,733,288 A | 3/1998 | Allen | |
| 5,741,253 A | 4/1998 | Michelson | |
| 5,741,261 A | 4/1998 | Moskovitz et al. | |
| 5,755,793 A | 5/1998 | Smith et al. | |
| 5,766,252 A | 6/1998 | Henry et al. | |
| 5,766,253 A | 6/1998 | Brosnahan, III | |
| 5,769,897 A | 6/1998 | Harle | |
| 5,776,197 A | 7/1998 | Rabbe et al. | |
| 5,776,198 A | 7/1998 | Rabbe et al. | |
| 5,776,199 A | 7/1998 | Michelson | |
| 5,782,830 A | 7/1998 | Farris | |
| 5,782,915 A | 7/1998 | Stone | |
| 5,782,917 A | 7/1998 | Carn | |
| 5,785,710 A | 7/1998 | Michelson | |
| 5,785,714 A | 7/1998 | Morgan et al. | |
| 5,797,871 A | 8/1998 | Wolfinbarger, Jr. | |
| 5,798,096 A | 8/1998 | Pavlyk | |
| 5,810,819 A | 9/1998 | Errico et al. | |
| 5,814,084 A | 9/1998 | Grivas et al. | |
| 5,820,581 A | 10/1998 | Wolfinbarger, Jr. | |
| 5,824,078 A | 10/1998 | Nelson et al. | |
| 5,824,084 A | 10/1998 | Muschler | |

| | | | |
|---|---|---|---|
| 5,824,088 A | 10/1998 | Kirsch | |
| 5,861,043 A | 1/1999 | Carn | |
| 5,865,845 A | 2/1999 | Thalgott | |
| 5,865,848 A | 2/1999 | Baker | |
| 5,865,849 A | 2/1999 | Stone | |
| 5,868,749 A | 2/1999 | Reed | |
| 5,876,455 A | 3/1999 | Harwin | |
| 5,879,403 A | 3/1999 | Ostiguy et al. | |
| 5,885,292 A | 3/1999 | Moskovitz et al. | |
| 5,885,299 A | 3/1999 | Winslow et al. | |
| 5,888,222 A | 3/1999 | Coates et al. | |
| 5,888,224 A | 3/1999 | Beckers et al. | |
| 5,888,227 A | 3/1999 | Cottle | |
| 5,895,426 A | 4/1999 | Scarborough et al. | |
| 5,897,593 A | 4/1999 | Kohrs et al. | |
| 5,899,939 A | 5/1999 | Boyce et al. | |
| 5,899,941 A | 5/1999 | Nishijima et al. | |
| 5,902,338 A | 5/1999 | Stone | |
| 5,904,716 A | 5/1999 | Gendler | |
| 5,904,719 A | 5/1999 | Errico et al. | |
| 5,910,315 A | 6/1999 | Stevenson et al. | |
| 5,913,900 A | 6/1999 | Stone | |
| 5,919,196 A | 7/1999 | Bobic et al. | |
| 5,922,027 A | 7/1999 | Stone | |
| 5,935,169 A | 8/1999 | Chan | |
| 5,944,755 A | 8/1999 | Stone | |
| 5,968,047 A | 10/1999 | Reed | |
| 5,968,098 A | 10/1999 | Winslow | |
| 5,972,034 A | 10/1999 | Hofmann et al. | |
| 5,972,368 A | 10/1999 | McKay | |
| 5,976,187 A | 11/1999 | Richelsoph | |
| 5,980,522 A | 11/1999 | Koros et al. | |
| 5,981,828 A | 11/1999 | Nelson et al. | |
| 5,984,922 A | 11/1999 | McKay | |
| 5,984,967 A | 11/1999 | Zdeblick et al. | |
| 5,989,289 A * | 11/1999 | Coates et al. | 623/17.16 |
| 5,990,382 A | 11/1999 | Fox | |
| 5,997,580 A | 12/1999 | Mastrorio et al. | |
| 5,997,581 A | 12/1999 | Khalili | |
| 6,005,161 A | 12/1999 | Brekke et al. | |
| 6,008,433 A | 12/1999 | Stone | |
| 6,013,853 A | 1/2000 | Athanasiou et al. | |
| 6,017,343 A | 1/2000 | Rogozinski | |
| 6,025,538 A | 2/2000 | Yaccarino, III | |
| 6,030,635 A | 2/2000 | Gertzman et al. | |
| 6,033,405 A | 3/2000 | Winslow et al. | |
| 6,033,438 A | 3/2000 | Bianchi et al. | |
| 6,037,519 A | 3/2000 | McKay | |
| 6,039,762 A | 3/2000 | McKay | |
| 6,045,554 A | 4/2000 | Grooms et al. | |
| 6,045,579 A | 4/2000 | Hochshuler et al. | |
| 6,045,580 A | 4/2000 | Scarborough et al. | |
| 6,049,025 A | 4/2000 | Stone et al. | |
| 6,053,916 A | 4/2000 | Moore | |
| 6,059,790 A | 5/2000 | Sand et al. | |
| 6,080,158 A | 6/2000 | Lin | |
| 6,080,193 A | 6/2000 | Hochshuler et al. | |
| 6,090,998 A | 7/2000 | Grooms et al. | |
| 6,096,080 A | 8/2000 | Nicholson et al. | |
| 6,096,081 A | 8/2000 | Grivas et al. | |
| 6,110,482 A | 8/2000 | Khouri et al. | |
| 6,111,164 A | 8/2000 | Rainey et al. | |
| 6,120,506 A | 9/2000 | Kohrs et al. | |
| 6,123,731 A | 9/2000 | Boyce et al. | |
| 6,143,030 A | 11/2000 | Schroder | |
| 6,143,033 A | 11/2000 | Paul et al. | |
| 6,156,070 A | 12/2000 | Incavo et al. | |
| 6,174,311 B1 | 1/2001 | Branch et al. | |
| 6,187,329 B1 | 2/2001 | Agrawal et al. | |
| 6,200,347 B1 | 3/2001 | Anderson et al. | |
| 6,206,923 B1 | 3/2001 | Boyd et al. | |
| 6,241,769 B1 | 6/2001 | Nicholson et al. | |
| 6,245,108 B1 | 6/2001 | Biscup | |
| 6,258,125 B1 | 7/2001 | Paul et al. | |
| 6,261,586 B1 | 7/2001 | McKay | |
| 6,270,528 B1 | 8/2001 | McKay | |
| 6,277,149 B1 | 8/2001 | Boyle et al. | |
| 6,371,988 B1 | 4/2002 | Pafford et al. | |
| 6,391,058 B1 | 5/2002 | Kuslich et al. | |
| 6,409,765 B1 | 6/2002 | Bianchi et al. | |
| 6,482,233 B1 | 11/2002 | Aebi et al. | |
| 6,494,883 B1 | 12/2002 | Ferree | |
| 6,500,206 B1 | 12/2002 | Bryan | |
| 6,511,509 B1 * | 1/2003 | Ford et al. | 623/23.5 |
| 6,520,993 B2 * | 2/2003 | James et al. | 623/17.16 |
| 6,551,355 B1 * | 4/2003 | Lewandrowski et al. | 623/16.11 |
| 6,554,863 B2 | 4/2003 | Paul et al. | |
| 6,695,882 B2 | 2/2004 | Bianchi et al. | |
| 6,827,740 B1 * | 12/2004 | Michelson | 623/17.11 |
| 6,986,788 B2 | 1/2006 | Paul et al. | |
| 7,282,063 B2 * | 10/2007 | Cohen et al. | 623/17.13 |
| 7,569,074 B2 * | 8/2009 | Eisermann et al. | 623/17.11 |
| 2001/0001129 A1 | 5/2001 | McKay et al. | |
| 2001/0010021 A1 | 7/2001 | Boyd et al. | |
| 2001/0014831 A1 | 8/2001 | Scarborough | |
| 2001/0016775 A1 | 8/2001 | Scarborough et al. | |
| 2001/0016777 A1 | 8/2001 | Biscup | |
| 2001/0049560 A1 * | 12/2001 | Paul et al. | 623/17.16 |
| 2002/0091447 A1 | 7/2002 | Shimp et al. | |
| 2002/0106393 A1 | 8/2002 | Bianchi et al. | |
| 2002/0107570 A1 | 8/2002 | Sybert et al. | |
| 2004/0230306 A1 | 11/2004 | Hoeck et al. | |
| 2005/0055098 A1 * | 3/2005 | Zdeblick et al. | 623/17.11 |
| 2006/0149376 A1 * | 7/2006 | Shimp et al. | 623/17.11 |
| 2006/0247770 A1 * | 11/2006 | Peterman | 623/17.11 |
| 2006/0247771 A1 * | 11/2006 | Peterman et al. | 623/17.11 |
| 2009/0312837 A1 * | 12/2009 | Eisermann et al. | 623/17.11 |

FOREIGN PATENT DOCUMENTS

| | | |
|---|---|---|
| DE | 42 42 889 | 6/1994 |
| DE | 44 23 257 | 1/1996 |
| DE | 299 13 200 | 10/1999 |
| EP | 0 366 029 | 5/1990 |
| EP | 0 505 634 | 9/1992 |
| EP | 0 517 030 | 12/1992 |
| EP | 0 520 237 | 12/1992 |
| EP | 0 538 183 | 4/1993 |
| EP | 0 577 178 | 1/1994 |
| EP | 0 639 351 | 2/1995 |
| EP | 0 646 366 | 4/1995 |
| EP | 0 966 930 | 12/1999 |
| FR | 2 552 659 | 4/1985 |
| FR | 2645748 | 10/1990 |
| FR | 2 717 068 | 9/1995 |
| GB | 2 220 571 | 1/1990 |
| JP | 178993 | 7/1988 |
| JP | 241461 | 9/1990 |
| JP | 271856 | 11/1990 |
| JP | 029663 | 2/1991 |
| JP | 614947 | 1/1994 |
| SU | 833226 | 5/1981 |
| SU | 1465040 | 3/1989 |
| WO | WO 94/26211 | 11/1994 |
| WO | WO 94/26213 | 11/1994 |
| WO | WO 95/08964 | 4/1995 |
| WO | WO 95/15133 | 6/1995 |
| WO | WO 96/11642 | 4/1996 |
| WO | WO 96/39988 | 12/1996 |
| WO | WO 97/14378 | 4/1997 |
| WO | WO 97/15248 | 5/1997 |
| WO | WO 97/25945 | 7/1997 |
| WO | WO 97/32547 | 9/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09914 | 3/1999 |
| WO | WO 99/13806 | 3/1999 |
| WO | WO 99/29271 | 6/1999 |
| WO | WO 99/32055 | 7/1999 |
| WO | WO 99/38461 | 8/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/40179 | 7/2000 |
| WO | WO 00/41654 | 7/2000 |
| WO | WO 00/42954 | 7/2000 |

| | | |
|---|---|---|
| WO | WO 00/59412 | 10/2000 |
| WO | WO 00/74607 | 12/2000 |
| WO | WO 00/74608 | 12/2000 |
| WO | WO 01/08611 | 2/2001 |

OTHER PUBLICATIONS

Joseph Catanese III et al., "Heterogeneity of the mechanical properties of demineralized bone," Journal of Biomechanics, vol. 32, pp. 1365-1369, 1999.

Kai-Uwe Lewandrowski et al., "Mechanical Properties of Perforated and Partially Demineralized Bone Grafts," Clinical Orthopaedics and Related Research, No. 353, pp. 238-246, 1998.

Kai-Uwe Lewandrowski et al., "Improved Osteoinduction of Cortical Bone Allografts: A Study of the Effects of Laser Perforation and Partial Demineralization," Journal of Orthopaedic Research, vol. 15, pp. 748-756, 1997.

Kai-Uwe Lewandrowski et al., "Kinetics of cortical bone demineralization: Controlled demineralization—a new method for modifying cortical bone allografts," Journal of Biomedical Materials Research, vol. 31, pp. 365-372, 1996.

Douglas W. Jackson et al., "Biological Remodeling after Anterior Cruciate Ligament Reconstruction Using a Collagen Matrix Derived from Demineralized Bone," American Journal of Sports Medicine, vol. 24, pp. 405-414, 1996.

Steven M. Bowman et al., "The Tensile Behavior of Demineralized Bovine Cortical Bone," J. Biomechanics, vol. 29, pp. 1497-1501, 1996.

K.K.J. Hallfeldt et al., "Sterilization of Partially Demineralized Bone Matrix: The Effects of Different Sterilization Techniques on Osteogenetic Properties," Journal of Surgical Research, vol. 59, pp. 614-620, 1995.

J.J. Broz et al., "Material and Compositional Properties of Selectively Demineralized Cortical Bone," J. Biomechanics, vol. 28, pp. 1357-1368, 1995.

Michael Centrella., "Transforming Growth Factor-.beta. Gene Family Members and Bone," Endocrine Reviews, vol. 15, pp. 27-39, 1994.

Torvard C. Laurent et al., "Hyaluronan," The FASEB Journal, vol. 6, pp. 2397-2404, 1992.

Christian Delloye et al., "Morphometric and Physical Investigations of Segmental Cortical Bone Autografts and Allografts in Canine Ulnar Defects," Clinical Orthopaedics and Related Research, No. 282, pp. 273-292, 1992.

Ma Zhen Guo et al., "The Mechanical and Biological Properties of Demineralised Cortical Bone Allografts in Animals," The Journal of Bone and Joint Surgery [Br], vol. 73-B, pp. 791-794, 1991.

Anthony J. Celeste et al., "Identification of transforming growth factor .beta. family members present in bone-inductive protein purified from bovine bone," Proc. Natl. Acad. Sci. USA, vol. 87, pp. 9843-9847, 1990.

Stanley G. Hopp et al., "A Study of the Mechanical Strength of Long Bone Defects Treated with Various Bone Autograft Substitutes: An Experimental Investigation in the Rabbit," Journal of Orthopaedic Research, vol. 7, pp. 579-584, 1989.

Reuven Gepstein et al., "Bridging Large Defects in Bone by Demineralized Bone Matrix in the Form of a Powder," The Journal of Bone and Joint Surgery, vol. 69-A, pp. 984-992, 1987.

J.J. Vandersteenhoven et al., "Histological investigation of bone induction by demineralized allogenic bone matrix: A natural biomaterial for osseous reconstruction," Journal of Biomedical Materials Research, vol. 17, pp. 1003-1014, 1983.

F. M. Eggert et al., "Rapid Demineralization in Acidic Buffers," Histochemistry, vol. 59, pp. 215-224, 1979.

Albert H. Burstein et al., "Contribution of Collagen and Mineral to the Elastic-Plastic Properties of Bone," The Journal of Bone and Joint Surgery, vol. 57-A, pp. 956-961, 1975.

A. H. Reddi et al., "Chemical Sequences in the Transformation of Normal Fibroblasts in Adolescent Rats," Proc. Nat. Acad. Sci. USA, vol. 69, pp. 1601-1605, 1972.

Marshall R. Urist, "Bone Formation by Autoinduction," Science, pp. 893-899, vol. 150, 1965.

* cited by examiner

DETAIL A

DETAIL B

IMPLANTABLE INTERVERTEBRAL FUSION DEVICE

FIELD OF THE INVENTION

The present invention relates generally to an implantable intervertebral fusion device and, more specifically, to allograft bone devices with an anatomical shape that effectively conforms to, and adheres to, the endplates of the adjacent vertebras. The present invention is also directed to methods of using a series of continuous footings and grooves for strong mechanical attachment to the patient bone tissue.

BACKGROUND

The vertebral column is a bio-mechanical arrangement composed largely of ligaments, muscles, vertebrae, and intervertebral discs. The bio-mechanical functions of the spine include: (1) support of the body, which involves the transfer of the weight and the bending movements of the head, trunk and arms to the pelvis and legs; (2) complex physiological motion between these parts; and (3) protection of the spinal cord and nerve roots.

As populations age, it is anticipated that there will be an increase in adverse spinal conditions which are characteristic of aging. For example, with aging comes an increase in the degeneration of the intervertebral disc. Disabling mechanical pain resulting from disc degeneration is often treated surgically with an interbody fusion.

The primary purpose of the intervertebral discs, located between the endplates of the adjacent vertebrae, is to distribute forces between vertebrae, stabilize the spine, and cushion vertebral bodies. Thus the intervertebral disc acts as a shock absorber for the spinal column. A normal intervertebral disc includes a semi-gelatinous component which is surrounded by an outer ring called the annulus fibrosus. In a healthy spine, the annulus fibrosus prevents the gelatinous component from protruding outside the disc space.

Spinal discs may be displaced or damaged as a result of disease, trauma, aging or injury to the spine. Frequently, the only relief from the disability caused by degenerated spinal discs is a discectomy, or surgical removal of the intervertebral disc followed by fusions of the adjacent vertebrae. The removal of the damaged or unhealthy disc without reconstruction would allow the disc space to collapse, resulting in further instability of the spine, abnormal joint mechanics, premature development of arthritis or nerve damage, in addition to severe pain. To prevent the intervertebral space from collapsing, a structure must be placed within the intervertebral space to provide support.

For example, in early spinal fusion techniques, bone material, or bone osteogenic fusion devices were simply placed between the transverse processes of adjacent vertebrae. The osteogenic fusion material consisted of cortical-cancellous bone which was not strong enough to support the weight of the spinal column at the instrumented level. Consequently, the spine was stabilized by way of a plate or a rod spanning the affected vertebrae.

For example, U.S. Pat. No. 4,604,995 assigned to Stephens, David C. and Morgan, Craig D., discloses "a surgical implant for imparting stability to the thoraco-lumbar spine by fixation of the implant to the spine with segmental spinal instrumentation, the implant comprising: a unitary rod having a generally rectangular configuration formed by a pair of spaced apart branches substantially mirror image duplicates of one another and substantially equally spaced apart along their entire length; a bight end piece interconnecting the branch pair at one end portion thereof; and a gate forming end piece connected to close the other end portion of the branch pair except for a small gate opening to provide access to the space between the branch pair."

With this technique, once the fusion occurs, the hardware maintaining the stability of the spine becomes superfluous. There are other several disadvantages associated with the use of the abovementioned metal implants. Solid body metal implants do not effectively enable bone in-growth which may lead to the eventual failure of the implant. Surface porosity in such solid implants does not correct this problem because it will not allow sufficient in-growth to provide a solid bone mass strong enough to withstand the loads of the spine. Attention was then turned to implants, or interbody fusion devices, which could be interposed between the adjacent vertebrae, maintain the stability of the disc interspace, and still permit fusion or arthrodesis.

For example, U.S. Pat. No. 4,961,740 assigned to Centerpulse USA Inc., discloses "a fusion cage adapted for promoting fusion of one or more bone structures when bone-growth-inducing substance is packed into the fusion cage, comprising: a cage body defining a cavity with an inner surface; said cavity adapted to be packed with the bone-growth-inducing substance; said cage body defining an outer surface; means for defining threads on the outer surface of the cage body and adapted for biting into the bone structure; said threads defining means including a plurality of threads which define valleys there between; a plurality of perforations provided in the valleys of the threads for providing communication between the outer surface and the cavity in order to allow immediate contact between the one or more bone structures and the bone-growth-inducing substance packed into the fusion cage".

U.S. Pat. No. 5,026,373 assigned to Surgical Dynamics, discloses "a method for surgically preparing two adjacent bony structures for implanting a hollow cylindrical fusion cage that has an external, substantially continuous helical thread which defines a plurality of turns with a valley between adjacent turns and that is perforated in the valley between adjacent turns of the thread, said method comprising the steps of: (a) drilling a pilot hole laterally between said bony structures, (b) inserting a pilot rod into the pilot hole, (c) fitting a hollow drill over the pilot rod, (d) with the hollow drill, enlarging said pilot hole to form a bore that penetrates into the cortical bone of each of said bony structures, and (e) tapping a female thread into the wall of said bore, the crown of which female thread penetrates into the cancellous portion of each of said bony structures, which female thread can mate with the helical thread of the fusion cage."

The abovementioned intervertebral fusion device has substantial disadvantages, however. The metallic supporting frame of the prior art fusion cages is not osteoconductive and therefore does not form a strong mechanical attachment to a patient's bone tissue. This can lead to graft necrosis, poor fusion and poor stability. Moreover, many of these devices are difficult to machine and therefore expensive. Furthermore, the fusion cages may stress shield the bone graft, increasing the time required for fusion to occur. The abovementioned implants further requires a special tool and additional preparation of the adjacent vertebral bodies to ensure fusion.

In addition, the use of bone graft materials in the prior art metal cage fusion devices presents several disadvantages. Autografts, bone material surgically removed from the patient, are undesirable because the donor site may not yield a sufficient quantity of graft material. The additional surgery to extract the autograft also increases the risk of infection, persistent pain, and may reduce structural integrity at the donor site.

U.S. Pat. No. 5,489,308 assigned to Zimmer Spine, Inc., discloses "an implant for insertion into a bore formed between opposing vertebrae of a spine where said vertebrae are separated by a spacing with a disk material having an annulus disposed within said spacing, said implant comprising: a rigid body having a leading end and a trailing end spaced apart by a longitudinal axis of said body; said body comprising at least exposed threads disposed at least partially between said leading end and said trailing end; said threads selected to engage vertebra material and draw said body along a direction of said axis upon rotation of said body about said axis; said body having a hollow, generally cylindrical shell with said threads disposed on an exterior surface of said shell; said body having means defining a chamber disposed within said body and said body is provided with a rib disposed within said cylindrical shell and extending radially inwardly toward said longitudinal axis, said rib dividing said chamber into a leading end chamber and a trailing end chamber, and said rib including at least a rigid extension extending between and connecting diametrically opposed sides of said body; said body having means defining at least one opening formed through said body in communication with said chamber and with said opening extending generally radially to said axis; and said body having a transverse dimension generally transverse to said longitudinal axis and dimensioned so as to be greater than said bore for said body to urge said opposing vertebrae apart and to stretch said annulus upon insertion of said body into said bore between said vertebrae with a portion of said body opposing a first of said opposing vertebrae and with an opposite side of said body opposing a second of said opposing vertebrae."

One problem with the implant devices of the type mentioned above is that they tend not to maintain the normal curvature of the spine. In a healthy state, the cervical and lumbar areas of the human spine curve convexly forward. Normal lordosis results, at least in significant measure, from the normal wedge-shaped nature of the spaces between adjacent pairs of the cervical and lumbar vertebrae, and the normal wedge-shaped nature of the intervertebral discs that fill these spaces. Loss of lordosis and proper intervertebral spacing may result in an increased risk of degeneration to other intervertebral discs located adjacent to the fusion level due to the alteration of the overall mechanics of the spine.

A further problem with the abovementioned implant is that the cylindrical geometry of the engaging element tends to provide a small area of contact between the engaging element and the vertebrae. The small engaging surface tends to contribute to subsidence or deformation of the cortical layer of the vertebrae adjacent to the engaging element. Moreover, the small engaging surface provides less contact between the bone graft material encased in the device and the adjacent vertebrae. Exposure of the bone graft material to the surface of the vertebrae is important because the greater the area of contact, the greater the possibility of having a successful fusion.

U.S. Pat. No. 6,143,033 discloses "an allogenic intervertebral implant for use when surgical fusion of vertebral bodies is indicated. The implant comprises an annular plug conforming in size and shape with the end plates of adjacent vertebrae and has a plurality of teeth positioned on the top and bottom surfaces for interlocking with the adjacent vertebrae. The teeth preferably have a pyramid shape or a saw-tooth shape." The teeth 105 of a prior art implant are shown in FIG. 1.

U.S. Pat. No. 6,986,788 discloses "an allogenic intervertebral implant for use when surgical fusion of vertebral bodies is indicated. The implant comprises a piece of allogenic bone conforming in size and shape with a portion of an end plates of the vertebrae and has a wedge-shaped profile with a plurality of teeth located on top and bottom surfaces." The teeth 205 of the implant 200 have a pyramidal shape, as shown in FIG. 2.

However, the implants are not sufficiently effective at preventing expulsion of the implant. The surfaces of the implants, whether pyramidal 205 or saw tooth 105, do not effectively provide implant stability.

In the light of the abovementioned disadvantages, there is a need for improved methods and systems that can provide effective, efficient and fast intervertebral fusion device. Specifically, an intervertebral implantable device is needed that conforms to the endplates of the patient's adjacent vertebrae, maintains the normal disc spacing, and appropriate curvature of the spine. Further, an approach is needed that maximizes the probability of success of bone fusion, provides instant stability to the spine while fusion occurs, is easily implantable, and minimizes trauma to the patient and the possibility of surgical and post-surgical complications.

SUMMARY OF THE INVENTION

The present invention relates to an implantable intervertebral fusion device for use when surgical fusion of vertebral bodies is indicated. The implant is comprised of bone conforming in size and shape with the end plates of the adjacent vertebrae and has a wedge-shaped profile with a plurality of footings and grooves located on the top and bottom surfaces.

In one embodiment, the invention is an implantable intervertebral device, comprising a bone body substantially conforming in size and shape with the endplates of adjacent vertebrae wherein, the bone body comprises a top surface and a bottom surface and wherein each of said top and bottom surface comprises a macro-structure having plurality of footings and grooves that define a space, said space being covered by a micro-structure.

Optionally, the micro-structure mimics cancellous bone architecture and/or has osteoconductive or osteoinductive qualities. The device is made of bone which is cut and machined into annular shapes.

Optionally, the space defined by the grooves and footings is at least 3 mm. Optionally, the footings comprise right triangles, have sharp ends, penetrate the endplates of the vertebrae, structurally degenerate to create an increased surface area for fusion, or have a minimum height of 0.5 mm.

Optionally, the grooves allow bone in-growth or are positioned at the front of each said footing. Optionally, the microstructure has a roughness of the order of 100-250 micrometers. Optionally, the top surface forms a convex curvature with its apex at the back of the bone body.

Optionally, the bone body has a wedge-shaped profile to adapt anatomically to a curvature of a plurality of lumbar vertebras endplates. Optionally, the bone body has a wedge-shaped profile to help restore disc space height and spine curvature. Optionally, an angle of the wedge shaped profile lies between 7° to 9°.

Optionally, the bottom surface is a flat planar surface. Optionally, the bone body has lateral corners which are rounded or chamfered. Optionally, the bone body has a back which is rounded or chamfered. Optionally, the bone body has at least one side with a lateral square guide for holding the bone body by a surgical instrument for anterior or anterior-lateral insertion.

Optionally, any of the devices have a bone body that comprises at least one of allograft bone or xenograft bone. Optionally, any of the devices can be used in any one of an ALIF, PLIF, ACF, or TLIF procedure.

BRIEF DESCRIPTION OF THE DRAWINGS

The invention will be better understood when consideration is given to the following detailed description thereof. Such description makes reference to the annexed drawings wherein.

DETAILED DESCRIPTION

The present invention relates to an implantable intervertebral fusion device for use when surgical fusion of vertebral bodies is indicated. The implant is comprised of an allogenic cortical bone conforming in size and shape with the end plates of the adjacent vertebrae and has a wedge-shaped profile with a plurality of footings and grooves located on the top and bottom surfaces.

The top and bottom surface of the implant has a macro-texture and a micro-texture. The macro-structure is formed by a series of continuous footings and grooves that cross the implant from side to side. The relative placement of each footing and groove defines a surface upon which an osteoconductive and/or osteoinductive micro-structure may be applied. The top surface of the implantable device is a convex surface with its apex at the back of the implant and the bottom surface is flat planar surface or curved surface to match the topography of the end plate.

The lateral corners of the implantable device are rounded or chamfered in order to adapt anatomically to the vertebrae endplates curvature. The back of the device is rounded or chamfered in order to facilitate insertion of the implant. In one embodiment, the implant has a lateral guide or groove on at least one side for receiving a surgical instrument for implantation. The guide or groove runs in lateral direction to accommodate a variety of surgical approaches. In another embodiment, resorbable and/or nonresorbable fixation devices, such as screws, could be placed on the endplates in front of the implant to improve initial fixation.

Figure 1:
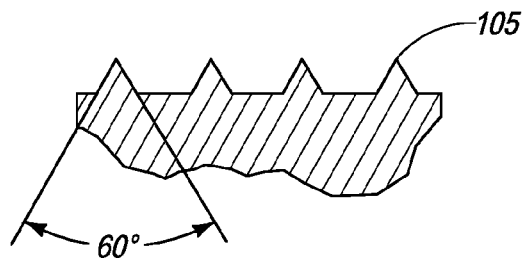
FIG. 1 is a side view of the teeth of a prior art implant.
Figure 2:
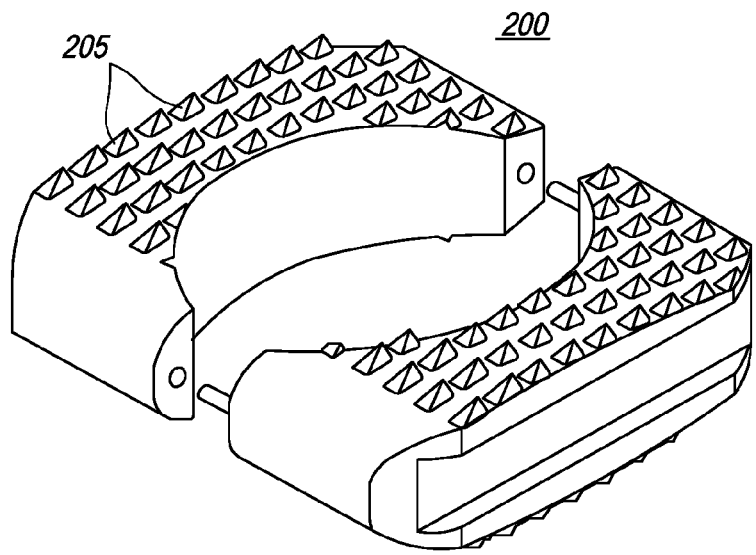
FIG. 2 is a perspective view of a prior art implant with pyramidal teeth.
Figure 3:
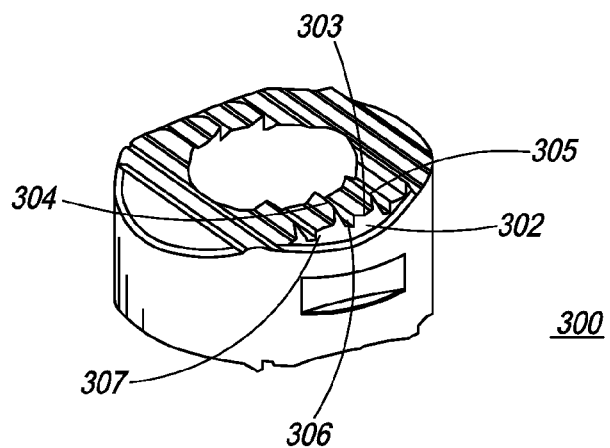
FIG. 3 is a perspective view of one embodiment of the intervertebral fusion device of the present invention.

Referring to FIG. 3, a top view of the first embodiment of the intervertebral fusion device according to the present invention is depicted. The intervertebral fusion device 300 conforms in size and shape with the end plates of the adjacent vertebrae between which the device 300 is to be implanted. The device 300 is made of an allograft material which helps in the formation of new bone to fuse the two vertebral bodies together. In one embodiment, the intervertebral fusion device 300 is used as an implant deployed in an Anterior Lumbar Interbody Fusion (ALIF) procedure. In another embodiment, the intervertebral fusion device 300 is used as an implant deployed in a Posterior Lumbar Interbody Fusion (PLIF) procedure. In yet another embodiment, the intervertebral fusion device 300 is used as an implant deployed in an Anterior Cervical Fusion (ACF) procedure. In yet another embodiment, the intervertebral fusion device 300 is used as an implant deployed in a Transforaminal Lumbar Interbody Fusion (TLIF) procedure. The intervertebral fusion device can be used in any region of the spine.

Figure 9:
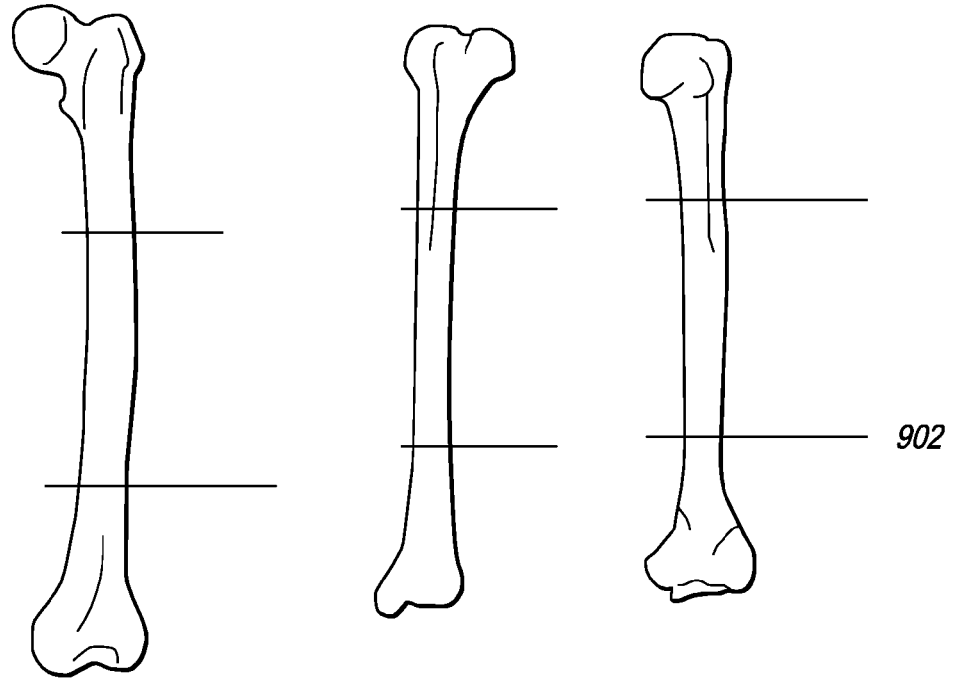
FIG. 9 is a set of bones that are used in the fabrication of the intervertebral fusion device of the present invention.
Figure 10:
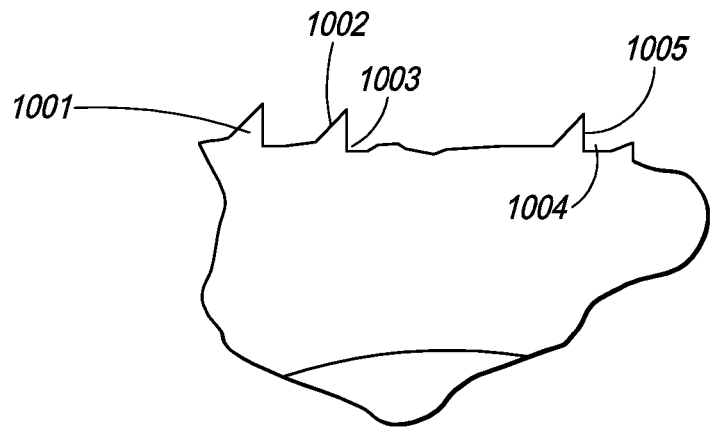
FIG. 10 is a schematic diagram depicting the footings and grooves of the implantable intervertebral fusion device of the present invention.

Referring to FIG. 9, a set of bones that are used in the fabrication of the abovementioned intervertebral fusion device is depicted. The bones can be from any source, including animals such as cows or pigs, e.g. xenograft bone. In one embodiment, the intervertebral fusion device is made of allogenic cortical bone received from human long bones. The pieces of these cortical long bones 900 are cut perpendicular 902 to the bone axis and the marrow is removed to obtain annular shapes. The annular rings are then machined using appropriate equipment, known to persons of ordinary skill in the art, and are finally cleaned for implantation.

Figure 4:
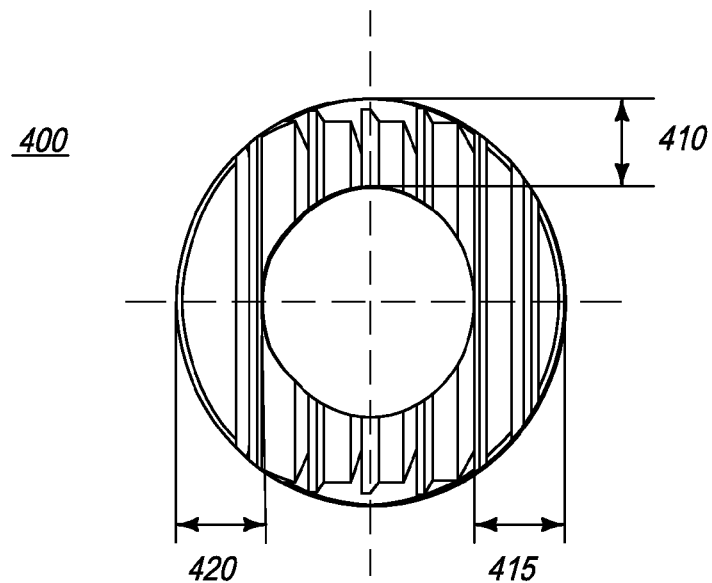
FIG. 4 is a top view of one embodiment of the intervertebral fusion device of the present invention.

Referring back to FIG. 3, the intervertebral fusion device 300 comprises a macro-structure 302 and a micro structure 303. The macro-structure 302 further comprises a plurality of footings 304, 305 and grooves 306, 307 that cross the intervertebral fusion device 300 from side to side. FIG. 4 depicts the general ring structure of the intervertebral fusion device. In one embodiment, the dimensions 410, 420, 415 can be of any size that would be appropriate for use in ACF, ALIF, and PLIF procedures. In another embodiment, dimensions 410, 420 range from 2 mm to 6 mm, preferably 4 mm, and dimension 415 ranges from 2 mm to 8 mm, preferably 6 mm.

Figure 5:
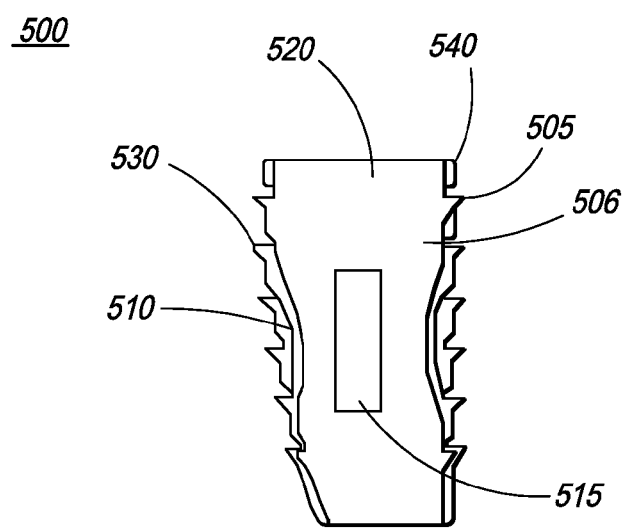
FIG. 5 is a side view of one embodiment of the intervertebral fusion device of the present invention.

Referring to FIG. 5, an implant 500 is shown. The implant 500 comprises a body 520 having a guide 515, a top surface 530, and a bottom surface 540. Optionally, at least one of the top or bottom surface comprises a convex depression 510 and a plurality of footings 505 and grooves 506 that form a macro-structure for enabling adhesion between the implant and surrounding bone. An osteoconductive and/or osteoinductive micro-structure, not shown, can be applied between the footings.

Figure 6:
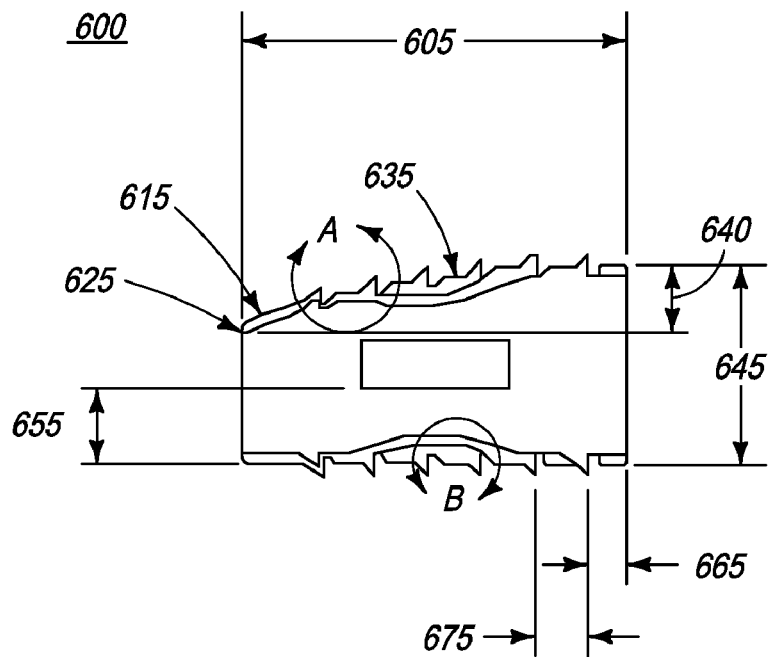
FIG. 6 is a side view one embodiment of the intervertebral fusion device of the present invention with details A and B.

FIGS. 6-8 and 10 disclose a plurality of exemplary embodiments of the macro-structure. FIG. 6 depicts an implant structure 600 having a macrostructure 635 which is more particularly shown in details A and B provided in FIGS. 7 and 8 respectively.

The implant structure can be described by a plurality of dimensions, namely the distance between the highest portion of the top surface and the lowest portion of the top surface 640; the anterior height 645; the anterior-posterior depth of the implant 605; the distance between footings 665; the roughness of the microtexture coating 665; the distance between the bottom surface and surgical instrument groove 655; the dome radius of certain structures 615, 625, 635 and the medio-lateral width (not shown). However, it should be appreciated that the values for these dimensions are not limiting and are provided as an enabling examples of how an implant could be practiced.

In one embodiment, an ALIF implant is designed with a distance of 2-6 mm between the highest portion of the top surface and the lowest portion of the top surface 640, which defines a lordosis angle of 5 to 13 degrees; a distance of 9-21 mm for the anterior height 645; a distance of 21-28 mm for the anterior-posterior depth of the implant 605; a distance of 2-6 mm between footings 665; a roughness of 100 to 250 microns for the microtexture coating 665; a distance of 3 mm to 9 mm between the bottom surface and surgical instrument groove 655; a dome radius of 0.1-2 mm, 20-40 mm, and for 80-110 mm for structures 625, 615, 635 respectively; and a distance of 24-32 mm for the medio-lateral width (not shown). The instrument groove can be defined as having a width no greater than one-third of the implant anterior height, which would yield a depth range of 3 mm to 7 mm in this example, and a depth no greater than a value which would leave the minimum implant wall thickness as at least 3 mm.

In one embodiment, a PLIF implant is designed with a distance of 0-3 mm between the highest portion of the top surface and the lowest portion of the top surface 640, which defines a lordosis angle of 0 to 7 degrees; a distance of 7-16 mm for the anterior height 645; a distance of 20-26 mm for the anterior-posterior depth of the implant 605; a distance of 2-6 mm between footings 665; a roughness of 100 to 250 microns for the microtexture coating 665; a distance of 3 mm to 9 mm between the bottom surface and surgical instrument groove 655; a dome radius of 0.1-2 mm, 20-40 mm, and for 80-110 mm for structures 625, 615, 635 respectively; and a distance of 7-11 mm for the medio-lateral width (not shown). The instrument groove can be defined as having a width no greater than one-third of the implant anterior height, which would yield a depth range of 2.33 mm to 5.33 mm in this example, and a depth no greater than a value which would leave the minimum implant wall thickness as at least 3 mm.

In one embodiment, an ACF implant is designed with a distance of 0-5 mm between the highest portion of the top surface and the lowest portion of the top surface 640, which defines a lordosis angle of 0 to 10 degrees; a distance of 4.5-12 mm for the anterior height 645; a distance of 10-14 mm for the anterior-posterior depth of the implant 605; a distance of 2-4 mm between footings 665; a roughness of 100 to 250 microns for the microtexture coating 665; a distance of 3 mm to 9 mm between the bottom surface and surgical instrument groove 655; a dome radius of 0.1-2 mm, 20-40 mm, and for 80-110 mm for structures 625, 615, 635 respectively; and a distance of 9-16 mm for the medio-lateral width (not shown). The instrument groove can be defined as having a width no greater than one-third of the implant anterior height, which would yield a depth range of 1.5 mm to 4 mm in this example, and a depth no greater than a value which would leave the minimum implant wall thickness as at least 3 mm.

Regardless of dimensions used, every adjacent footing 304 and groove 305 defines an area upon which an osteoconductive and/or osteoinductive micro-structure can be applied. The micro-structure preferably has a roughness of the order of 100-250 micrometer, although other roughness ranges, such as 50 to 1000 microns, may be employed. This microstructure helps improve the initial stability of the intervertebral fusion device due to increased friction. The osteoconductive and/or oasteoinductive nature of the microtexture helps in the promotion of bone apposition. In one embodiment, the microtexture comprises the coating described in U.S. Pat. No. 4,206,516, which is incorporated herein by reference. In another embodiment, the microtexture comprises the coating described in U.S. Pat. No. 4,865,603, which is also incorporated herein by reference. In one embodiment, the microstructure mimics cancellous bone architecture.

Figure 7:
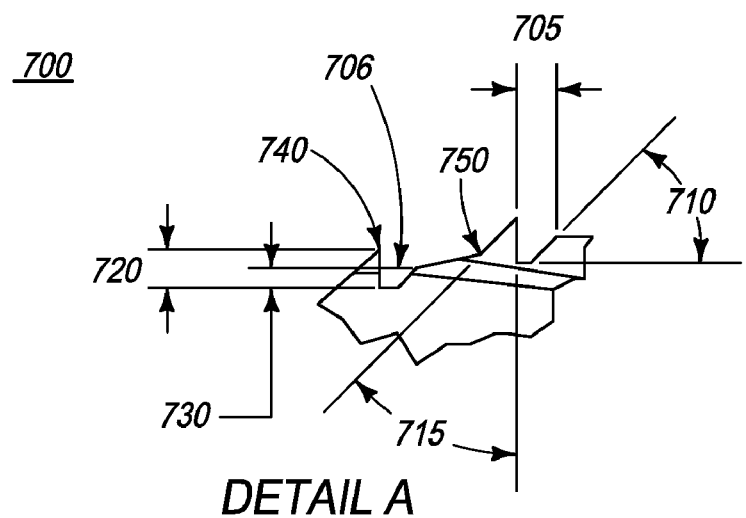
FIG. 7 is a side view of detail A from FIG. 6.
Figure 8:
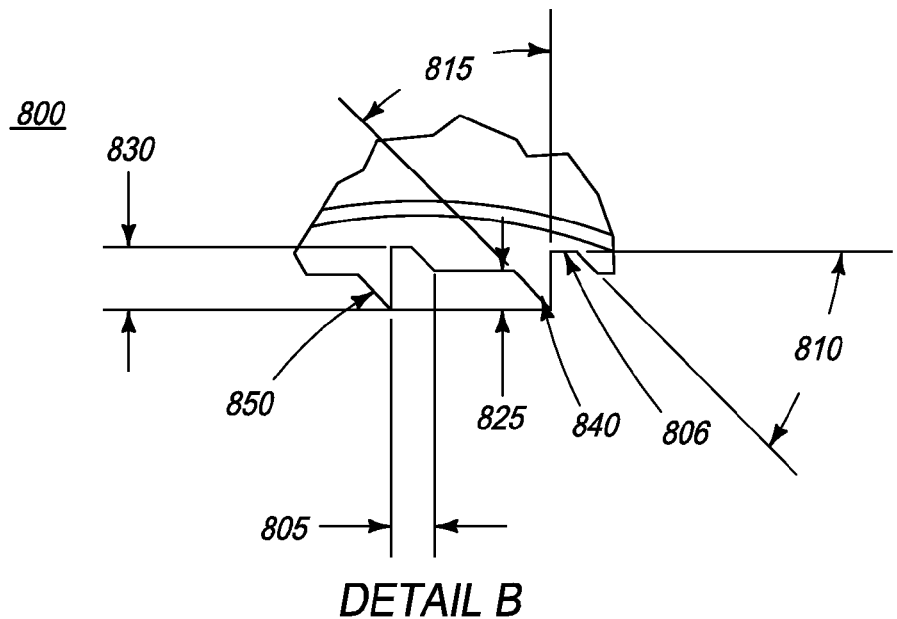
FIG. 8 is a side view of detail B from FIG. 6.

Now referring to FIGS. 7 and 8, the diagram depicts the footings and groove of the abovementioned implantable intervertebral fusion device. The footings 740, 750, 840, 850 have sharp protrusions which assist in the penetration of the intervertebral fusion device into the vertebras endplates and helps in the initial fixation of the implant. The initial mechanical stability attained by the footings 740, 750, 840, 850 minimizes the risk of post-operative expulsion of the implant. The grooves 705, 706, 805, 806 adjacent to the footings 740, 750, 840, 850 provide the long term fixation, after bone ingrowth happens in the grooves 705, 706, 805, 806. The footings 740, 750, 840, 850 in unison with the grooves 705, 706, 805, 806 provide mechanical interlocks between the intervertebral fusion device and the endplates of the vertebrae. In one embodiment of the present invention, by fixing a minimum separation between the footings 740, 750, 840, 850 the number of footings on the surface of the implant is reduced. Therefore, the points of contact with the endplates are also reduced which enables higher penetration of the footings 740, 750, 840, 850 into the endplates of the vertebrae.

In one embodiment, the footings 740, 840 have triangular protrusions with tips defined by angle 815 of 35 to 45 degrees. In another embodiment, the footings 740, 840 have a height 720 of 0.3 to 0.7 mm. In another embodiment, the footings 750, 850 comprise a first portion with a minimum predefined elevation 730 above the groove. In another embodiment, the footings 750, 850 have a second portion with a minimum predefined elevation 830 and a triangular protrusion with a tip defined as being in the range 715 of 35 to 45 degrees. It should be appreciated that, relative to the face of the implant, the footing protrusions are at right angles or tilted forward to ensure the implant resists expulsion by the vertebrae. This geometry of the teeth helps in preventing movement toward the front of the implant.

Figure 17A:
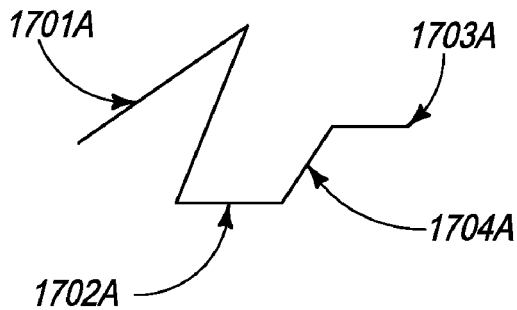
FIGS. 17A, 17B, and 17C are various configurations of footings that can be used in the present invention.
Figure 17B:
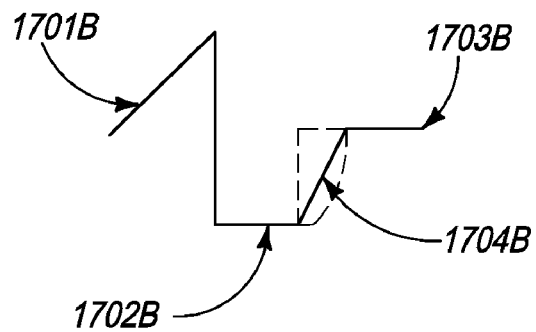

In another embodiment, the footing is an elevated structure with a sharp portion thereto and defined by at least one angle 715, 815 in the range of 15 to 65 degrees. Referring to FIGS. 17A to 17B, alternative footing designs are shown. In one embodiment, shown in FIG. 17A, a first footing 1701A has a triangular shape at an angle of less than 90 degrees relative to the groove surface 1702A. Groove 1702A separates the first footing 1701A from a second footing 1703A. The second footing 1703A has a protrusion with a face 1704A forming an angle of more than 135 degrees relative to the groove surface. In another embodiment, shown in FIG. 17B, a first footing 1701B has a triangular shape at a right angle relative to the groove surface 1702B. Groove 1702B separates the first footing 1701B from a second footing 1703B. The second footing 1703B has a protrusion with a face 1704B forming an angle of approximately 145 degrees relative to the groove surface 1702B.

Figure 17C:
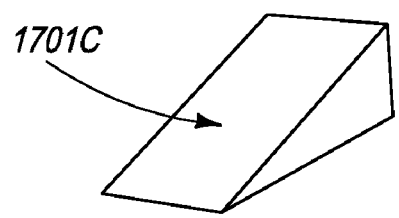

In another embodiment, at least one footing is in the shape of a pyramid and are right triangles with the opposite angles at 45° and its hypotenuse facing the back of the implant. In another embodiment, the footing 1701C has a triangular shape, shown in FIG. 17C. Alternatively, footings may have a saw tooth shape with the saw tooth running in the anterior-posterior direction. For any given implant, the number of footings can be in the range of 4 to 8, although there is no limitation on the specific number of footings per implant.

It should be appreciated that, in one embodiment, the footings are designed to structurally degenerate, i.e. crumble, after implant insertion, thereby increasing the surface area for fusion.

Figure 11:
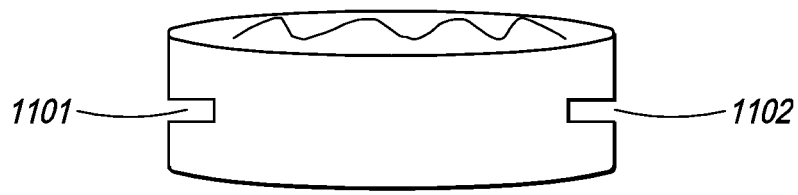
FIG. 11 is a schematic diagram depicting a set of lateral guides of the implantable intervertebral fusion device of the present invention.

Referring to FIG. 11, a first lateral guide and the second lateral guide of the abovementioned implantable intervertebral fusion device is depicted. The first lateral guide 1101 and the second lateral guide 1102 are sized to receive surgical instrument such as an inserter for implantation of implant. The first 1101 and second lateral guides 1102 can be of any geometric shape. In one embodiment, they are rectangular. In another embodiment, the lateral guides 1101, 1102 are 1 mm deep and 3 mm wide. In another embodiment, the lateral guides 1101, 1102 are of any size that allows an intervertebral fusion device to be grasped by the implantation instrument.

Figure 12:
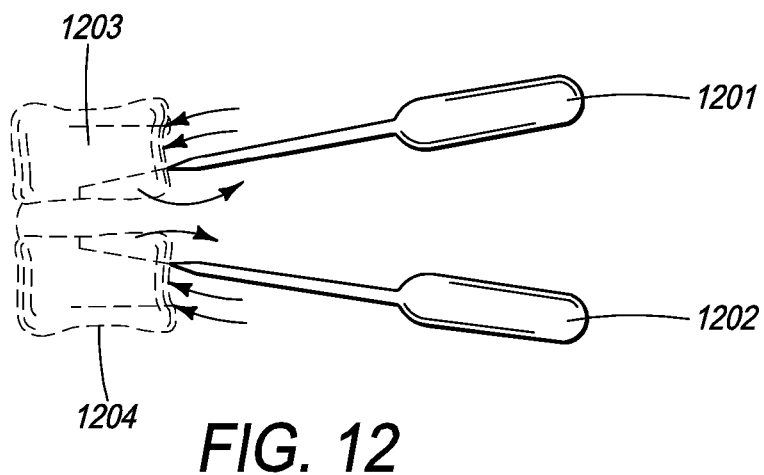
FIG. 12 is a schematic diagram of one embodiment of the surgical instrument for implanting intervertebral fusion device of the present invention.

Referring to FIG. 12, one embodiment of the implantation instrument for implanting the abovementioned intervertebral fusion device is depicted. The instrument comprises of handles 1201, 1202, and a set of two hooks 1203, 1204 at the extreme end for grasping the lateral guides. Once the surgeon is able to grip the lateral guides of the implant, the placement of the implant in the spinal column is carried out. In one embodiment, resorbable screws could be placed on the endplates in front of the implant to improve initial fixation.

The dimensions of implant can be varied to accommodate a patient's anatomy. However, the intervertebral fusion device of the present invention is preferably wide enough to support adjacent vertebrae and is of sufficient height to separate the adjacent vertebrae.

In one embodiment, a smaller implant would have a width of 27 mm and the front to back length of 25 mm and a larger implant would preferably have a width of 32 mm and front to back length of 28 mm. The size of the implant allows implants to be implanted using conventional open surgical procedures or minimally invasive procedures, such as laparoscopic surgery or an ALIF procedure. This minimizes muscle stripping, scar tissue in the canal, and nerve root retraction and handling. In addition, because the width is kept to a restricted size range and does not necessarily increase with implant height, taller implants can be used without requiring wider implants. Thus, facet removal and retraction of nerve roots can remain minimal.

In order to restore the natural curvature of the spine after the affected disc has been removed, the intervertebral fusion device of the present invention has a wedge-shaped profile.

Figure 13:
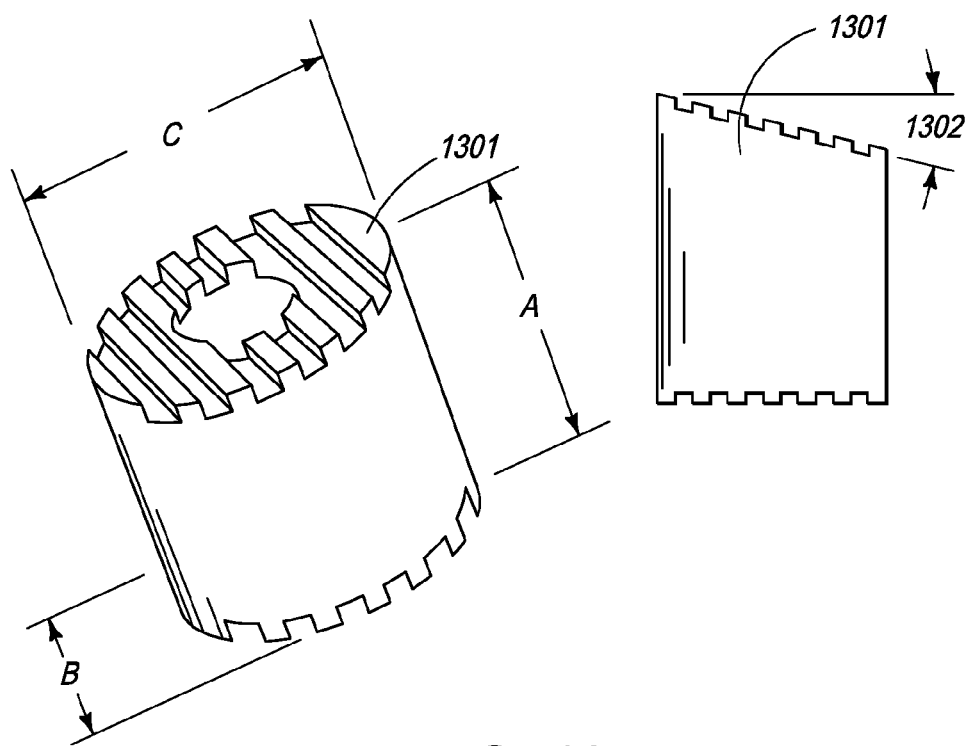
FIG. 13 depicts the wedge shaped profile of the intervertebral fusion device of the present invention.

Now referring to FIG. 13, one embodiment of the wedge shape profile of the intervertebral fusion device of the present invention is depicted. The wedge shape 1301 of the device results from a gradual decrease in the height from the front side to the back side. Thus, when implant is employed in the lumbar region, in one embodiment, the angle 1302 formed by the wedge is preferably between 7° to 9°, so that the wedge shape can mimic the anatomy of the lumbar spine and it can adapt anatomically to the curvature of the endplates of the lumbar vertebras.

In addition, to facilitate the insertion of implant and to adapt anatomically to the curvature of the vertebrae endplates, the lateral corners of the device are rounded or chamfered. The rounded or chamfered edges enable the intervertebral fusion device to slide between the endplates while minimizing the necessary distraction of the endplates.

Figure 14:
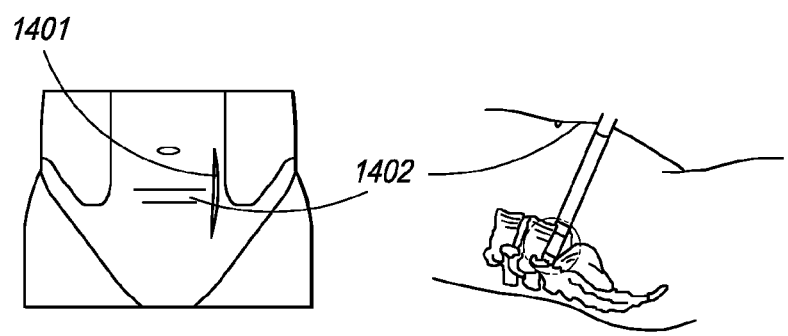
FIG. 14 depicts an anterior lumbar interbody fusion (ALIF) surgery for the implantation of the intervertebral fusion device of the present invention.

Referring to FIG. 14, an anterior lumbar interbody fusion surgery for the implantation of intervertebral fusion device of the present invention is depicted. The retroperitoneal approach for an ALIF procedure involves an incision 1401 on the left side of the abdomen 1402 and the abdominal muscles are retracted to the side. Since the anterior abdominal muscle in the midline (rectus abdominis) runs vertically, it does not need to be cut and easily retracts to the side. The abdominal contents lay inside a large sack (peritoneum) that can also be retracted, thus allowing the spine surgeon to access the front of the spine for implantation. In an alternate embodiment, endoscope procedure which involves surgery via several incisions can also be performed.

Figure 15:
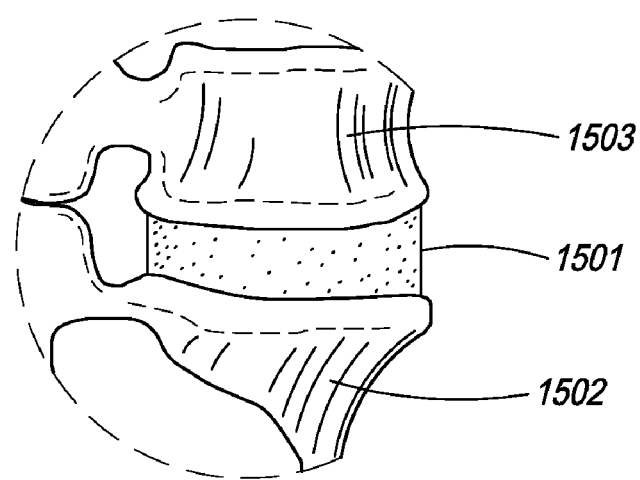
FIG. 15 depicts the fusion of the new bone after the implantation of the intervertebral fusion device of the present invention has taken place.

Although the intervertebral fusion device is a solid piece of allogenic cortical bone, the device can be provided with a hollow interior to form an interior space. This interior space can be filled with bone chips or any other osteoconductive surfacing or surface treatment, osteoinductive or any other bone growth stimulation coating material to further promote the formation of new bone. For example, FIG. 15 depicts the fusion of the new bone with the adjacent vertebrae after the implantation of intervertebral fusion device has taken place. The intervertebral fusion device 1501 is sandwiched between the adjacent vertebrae 1502, 1503 and the gradual bone in-growth takes place initially into the grooves of the device, and ultimately replaces the allograft bone structure.

Figure 16:
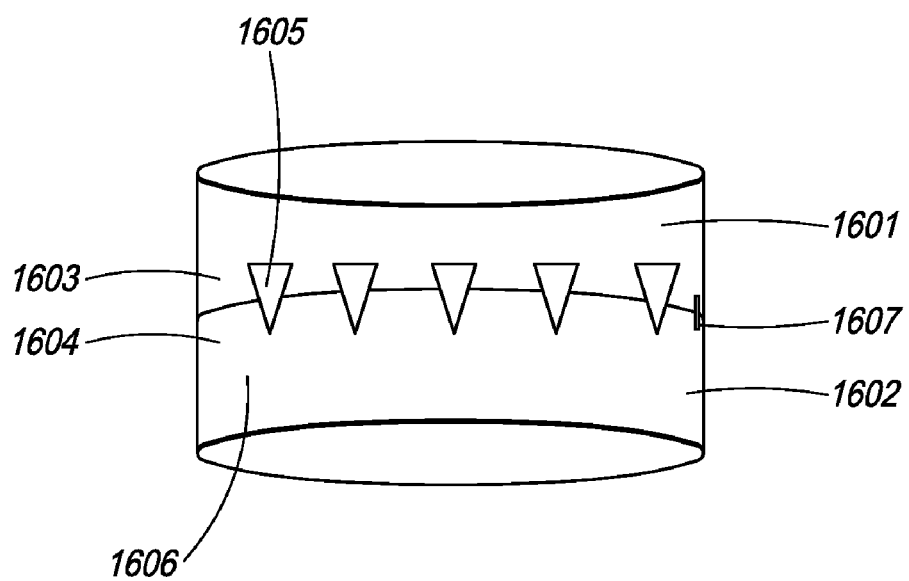
FIG. 16 depicts a side schematic view of another embodiment of the intervertebral fusion device of the present invention.

Referring to FIG. 16, a top view of another embodiment of the intervertebral fusion device of the present invention is depicted. In situations, where it is difficult to obtain a single section of allogenic bone from which the implant is to be made, fabricating implant in two pieces, i.e. top 1601 and bottom portions 1602, allows smaller sections of allogenic cortical bone to be used. A top connecting surface 1603 and a bottom connecting surface 1604 define the interface between the top 1601 and bottom 1602 portions.

As shown in the FIG. 16, the top 1601 and bottom 1602 surfaces, have ridges 1605 that mate with the grooves 1606 to interlock the top and bottom portions 1601, 1602. Preferably, ridges 1605 and grooves 1606 are formed by milling top and bottom surfaces 1603, 1604 in a first direction and then milling a second time with top and bottom surfaces 1603, 1604 oriented with respect to the first direction. A pin 1607 passing through aligned holes in top and bottom portions 1601, 1602 serves to retain top and bottom portions 1601, 1602 together. Although pin 1607 can be made of any biocompatible material, pin 1607 is preferably made of an allogenic bone. The number and orientation of pins 1607 can be varied.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

We claim:

1. An implantable intervertebral device, comprising: a bone body substantially conforming in size and shape with the endplates of adjacent vertebrae wherein, the bone body comprises a top surface and a bottom surface and wherein each of said top and bottom surface comprises a plurality of macro-structures extending from a first end of said bone body to a second end of said bone body, each of said macro-structures having a first footing with a height, a second footing with a height relative to the top surface of the bone body or bottom surface of the bone body, and a groove that defines a space between said first footing and said second footing, wherein the height of the first footing is greater than the height of the second footing and the first footing has a tip defined by an angle in a range of 15 degrees to 65 degrees and wherein the second footing of each macro-structure on said top surface of the bone body has a substantially flat top surface relative to the top surface of the bone body.

2. The device of claim 1 wherein a surface of the groove is made of cortical bone.

3. The device of claim 2 wherein the cortical bone surface has osteoconductive or osteoinductive qualities.

4. The device of claim 2, wherein the cortical bone surface has a roughness of the order of 100-250 micrometers.

5. The device of claim 1, wherein said bone body is cut from cortical bone and is machined into annular shapes.

6. The device of claim 1, wherein said space is equal to at least 3 mm.

7. The device of claim 1, wherein at least one of said first or second footings comprise right triangles.

8. The device of claim 1 wherein said first footing structurally degenerates to create an increased surface area for fusion.

9. The device of claim 1, wherein at least one of said first or second footings has a minimum height of 0.5 mm.

10. The device of claim 1, wherein said groove allows bone in-growth.

11. The device of claim 1, wherein said groove is positioned at the front of at least one of said first or second footings.

12. The device of claim 1, wherein the top surface forms a convex curvature with its apex at a back of said bone body.

13. The device of claim 1, wherein the bone body has a wedge-shaped profile to adapt anatomically to a curvature of a plurality of lumbar vertebras endplates.

14. The device of claim 1, wherein the bone body has a wedge-shaped profile to help restore disc space height and spine curvature.

15. The device of claim 14, wherein an angle of the said wedge shaped profile lies between 7° to 9°.

16. The device of claim 1, wherein the bottom surface is a flat planar surface.

17. The device of claim 1, wherein the bone body has lateral corners which are rounded or chamfered.

18. The device of claim 1, wherein the bone body has a back which is rounded or chamfered.

19. The device of claim 1, wherein the bone body has at least one side with a lateral square guide for holding the bone body by a surgical instrument for anterior or anterior-lateral insertion.

20. Any of the devices of claims 1 to 19, wherein the bone body comprises at least one of allograft bone or xenograft bone.

21. Any of the devices of claims 1 to 19, wherein the device is used in any one of an ALIF, PLIF, ACF, or TLIF procedure.

22. An implantable intervertebral device, comprising: a bone body substantially conforming in size and shape with the endplates of adjacent vertebrae wherein, the bone body comprises a top surface and a bottom surface and wherein each of said top and bottom surface comprises a plurality of macro-structures extending from a first end of said bone body to a second end of said bone body, each of said macro-structures having a first footing with a height, a second footing with a height relative to the top surface of the bone body or bottom surface of the bone body, and a groove that defines a space between said first footing and said second footing, wherein a surface of the groove is made of cortical bone having a roughness of the order of 50-1000 micrometers, wherein the surface has osteoconductive or osteoinductive qualities, wherein the height of the first footing is greater than the height of the second footing and the first footing has a tip defined by an angle in a range of 15 degrees to 65 degrees, and wherein the second footing of each macro-structure on said top surface of the bone body has a substantially flat top surface relative to the top surface of the bone body.

23. An implantable intervertebral device, comprising: a bone body substantially conforming in size and shape with the endplates of adjacent vertebrae wherein, the bone body comprises a top surface having a convex curvature with its apex at a back of said bone body and a bottom surface and wherein each of said top and bottom surface comprises a plurality of macro-structures extending from a first end of said bone body to a second end of said bone body, each of said macro-structures having a first portion with a height, a second portion with a height relative to the top surface of the bone body or bottom surface of the bone body, and a groove that defines a space between said first footing and said second footing, wherein a surface of the groove is made of cortical bone having a roughness of the order of 50-1000 micrometers, wherein the height of the first portion is greater than the height of the second portion and the first portion has a tip defined by an angle in a range of 15 degrees to 65 degrees, and wherein the second portion of each of said macro-structures on said top surface of the bone body has a substantially flat top surface relative to the top surface of the bone body.

* * * * *